(12) United States Patent
Glerum et al.

(10) Patent No.: US 9,848,997 B2
(45) Date of Patent: Dec. 26, 2017

(54) EXPANDABLE FUSION DEVICE AND METHOD OF INSTALLATION THEREOF

(71) Applicant: GLOBUS MEDICAL, INC., Audubon, PA (US)

(72) Inventors: Chad Glerum, Pennsburg, PA (US); Sean Suh, Morganville, NJ (US); Jody L. Seifert, Birdsboro, PA (US)

(73) Assignee: Globus Medical, Inc., Audubon, PA (US)

(*) Notice: Subject to any disclaimer, the term of this patent is extended or adjusted under 35 U.S.C. 154(b) by 0 days.

(21) Appl. No.: 15/255,250

(22) Filed: Sep. 2, 2016

(65) Prior Publication Data

US 2016/0374824 A1 Dec. 29, 2016

Related U.S. Application Data

(60) Division of application No. 14/179,178, filed on Feb. 12, 2014, now Pat. No. 9,456,903, which is a
(Continued)

(51) Int. Cl.
*A61F 2/44* (2006.01)
*A61F 2/30* (2006.01)

(52) U.S. Cl.
CPC .............. *A61F 2/447* (2013.01); *A61F 2/442* (2013.01); *A61F 2002/3052* (2013.01); *A61F 2002/3055* (2013.01); *A61F 2002/30387* (2013.01); *A61F 2002/30405* (2013.01); *A61F 2002/30492* (2013.01); *A61F 2002/30507* (2013.01); *A61F 2002/30523* (2013.01); *A61F 2002/30551* (2013.01); *A61F 2002/30578* (2013.01); *A61F 2002/30579* (2013.01); *A61F 2002/30841* (2013.01); *A61F 2002/30904* (2013.01); *A61F 2002/4475* (2013.01); *A61F 2220/0016* (2013.01); *A61F 2250/0009* (2013.01); *A61F 2310/00017* (2013.01); *A61F 2310/00023* (2013.01); *A61F 2310/00179* (2013.01)

(58) Field of Classification Search
CPC .......... A61F 2/44; A61F 2/4455; A61F 2/446; A61F 2/4465; A61F 2/447
USPC .................................. 623/17.11, 17.15, 17.16
See application file for complete search history.

(56) References Cited

U.S. PATENT DOCUMENTS 6,080,193 A   6/2000   Hochshuler
6,126,689 A   10/2000  Brett
(Continued)

FOREIGN PATENT DOCUMENTS

FR   2794968 A1   12/2000
FR   2874814 A1   3/2006
(Continued)

*Primary Examiner* — Si Ming Ku

(57) ABSTRACT

The present invention provides an expandable fusion device capable of being installed inside an intervertebral disc space to maintain normal disc spacing and restore spinal stability, thereby facilitating an intervertebral fusion. In one embodiment, the fusion device includes a body portion, a first endplate, and a second endplate, the first and second endplates capable of being moved in a direction away from the body portion into an expanded configuration or capable of being moved towards the body portion into an unexpanded configuration. The fusion device is capable of being deployed and installed in both configurations.

18 Claims, 15 Drawing Sheets

Related U.S. Application Data continuation of application No. 12/823,736, filed on Jun. 25, 2010, now Pat. No. 8,685,098.

(56) References Cited

U.S. PATENT DOCUMENTS

| | | |
|---|---|---|
| 6,176,882 B1 | 1/2001 | Biedermann |
| 6,558,423 B1 | 5/2003 | Michelson |
| 6,814,756 B1 | 11/2004 | Michelson |
| 7,951,199 B2 | 5/2011 | Miller |
| 8,062,375 B2 | 11/2011 | Glerum |
| 8,137,405 B2 | 3/2012 | Kostuik |
| 2002/0068976 A1 | 6/2002 | Jackson |
| 2002/0068977 A1 | 6/2002 | Jackson |
| 2004/0030387 A1 | 2/2004 | Landry |
| 2004/0153065 A1 | 8/2004 | Lim |
| 2005/0021145 A1 | 1/2005 | de Villiers |
| 2005/0080422 A1 | 4/2005 | Otte |
| 2005/0113916 A1 | 5/2005 | Branch |
| 2006/0015184 A1 | 1/2006 | Winterbottom |
| 2006/0084986 A1 | 4/2006 | Grinberg |
| 2006/0142859 A1 | 6/2006 | McLuen |
| 2006/0149385 A1 | 7/2006 | McKay |
| 2006/0241770 A1 | 10/2006 | Rhoda |
| 2007/0270968 A1 | 11/2007 | Baynham |
| 2008/0114467 A1 | 5/2008 | Capote |
| 2008/0140207 A1 | 6/2008 | Olmos |
| 2008/0147194 A1 | 6/2008 | Grotz |
| 2008/0221694 A1 | 9/2008 | Warnick |
| 2009/0024217 A1 | 1/2009 | Levy |
| 2009/0076616 A1 | 3/2009 | Duggal |
| 2010/0049324 A1 | 2/2010 | Valdevit |
| 2010/0211176 A1 | 8/2010 | Greenhalgh |
| 2010/0222816 A1 | 9/2010 | Gabelberger |
| 2010/0286783 A1 | 11/2010 | Lechmann |
| 2010/0292796 A1* | 11/2010 | Greenhalgh ....... A61B 17/8858 623/17.11 |
| 2011/0035011 A1 | 2/2011 | Cain |
| 2011/0093074 A1 | 4/2011 | Glerum |
| 2011/0160861 A1 | 6/2011 | Jimenez |
| 2011/0172774 A1 | 7/2011 | Varela |
| 2011/0184522 A1 | 7/2011 | Melkent et al. |
| 2011/0276142 A1 | 11/2011 | Niemiec |
| 2011/0301713 A1 | 12/2011 | Theofilos |
| 2011/0319997 A1 | 12/2011 | Glerum |
| 2012/0035729 A1 | 2/2012 | Glerum |
| 2012/0059470 A1 | 3/2012 | Weiman |
| 2012/0059472 A1 | 3/2012 | Weiman |
| 2012/0109308 A1 | 5/2012 | Lechmann |
| 2012/0130496 A1 | 5/2012 | Duffield |
| 2012/0165945 A1 | 6/2012 | Hansell |
| 2012/0185049 A1 | 7/2012 | Varela |
| 2012/0209386 A1 | 8/2012 | Triplett |
| 2012/0215313 A1 | 8/2012 | Saidha |
| 2012/0265309 A1 | 10/2012 | Glerum |
| 2012/0277870 A1 | 11/2012 | Wolters |
| 2012/0323329 A1 | 12/2012 | Jimenez |
| 2012/0330426 A1 | 12/2012 | McLaughlin |
| 2013/0023993 A1 | 1/2013 | Weiman |
| 2013/0023994 A1 | 1/2013 | Glerum |
| 2013/0158669 A1 | 6/2013 | Sungarian |

FOREIGN PATENT DOCUMENTS

| | | |
|---|---|---|
| JP | 2000-513263 A | 10/2000 |
| WO | 9942062 A1 | 8/1999 |
| WO | 9966867 A1 | 12/1999 |
| WO | 0245625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2012031267 A1 | 3/2012 |

* cited by examiner

EXPANDABLE FUSION DEVICE AND METHOD OF INSTALLATION THEREOF

CROSS REFERENCE TO RELATED APPLICATIONS

This application is a divisional of U.S. application Ser. No. 14,179,178, filed Feb. 12, 2014, which is a continuation of U.S. application Ser. No. 12/823,736 filed on Jun. 25, 2010, which are incorporated herein in their entireties for all purposes.

FIELD OF THE INVENTION

The present invention relates to the apparatus and method for promoting an intervertebral fusion, and more particularly relates to an expandable fusion device capable of being inserted between adjacent vertebrae to facilitate the fusion process.

BACKGROUND OF THE INVENTION

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, present methods for installing a conventional fusion device often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for a fusion device capable of being installed inside an intervertebral disc space at a minimum to no distraction height and for a fusion device that can maintain a normal distance between adjacent vertebral bodies when implanted.

SUMMARY OF THE INVENTION

In an exemplary embodiment, the present invention provides an expandable fusion device capable of being installed inside an intervertebral disc space to maintain normal disc spacing and restore spinal stability, thereby facilitating an intervertebral fusion. In one embodiment, the fusion device includes a body portion, a first endplate, and a second endplate. The first and second endplates are capable of being moved in a direction away from the body portion into an expanded configuration or capable of being moved towards the body portion into an unexpanded configuration. The expandable fusion device is capable of being deployed and installed in the unexpanded configuration or the expanded configuration.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

A spinal fusion is typically employed to eliminate pain caused by the motion of degenerated disk material. Upon successful fusion, a fusion device becomes permanently fixed within the intervertebral disc space. Looking at FIG. 1, an exemplary embodiment of an expandable fusion device 10 is shown between adjacent vertebral bodies 2 and 3. The fusion device 10 engages the endplates 4 and 5 of the adjacent vertebral bodies 2 and 3 and, in the installed position, maintains normal intervertebral disc spacing and restores spinal stability, thereby facilitating an intervertebral fusion. The expandable fusion device 10 can be manufactured from a number of materials including titanium, stainless steel, titanium alloys, non-titanium metallic alloys, polymeric materials, plastics, plastic composites, PEEK, ceramic, and elastic materials.

In an exemplary embodiment, bone graft or similar bone growth inducing material can be introduced around and within the fusion device 10 to further promote and facilitate the intervertebral fusion. The fusion device 10, in one embodiment, is preferably packed with bone graft or similar bone growth inducing material to promote the growth of bone through and around the fusion device. Such bone graft may be packed between the endplates of the adjacent vertebral bodies prior to, subsequent to, or during implantation of the fusion device.

Figure 2:
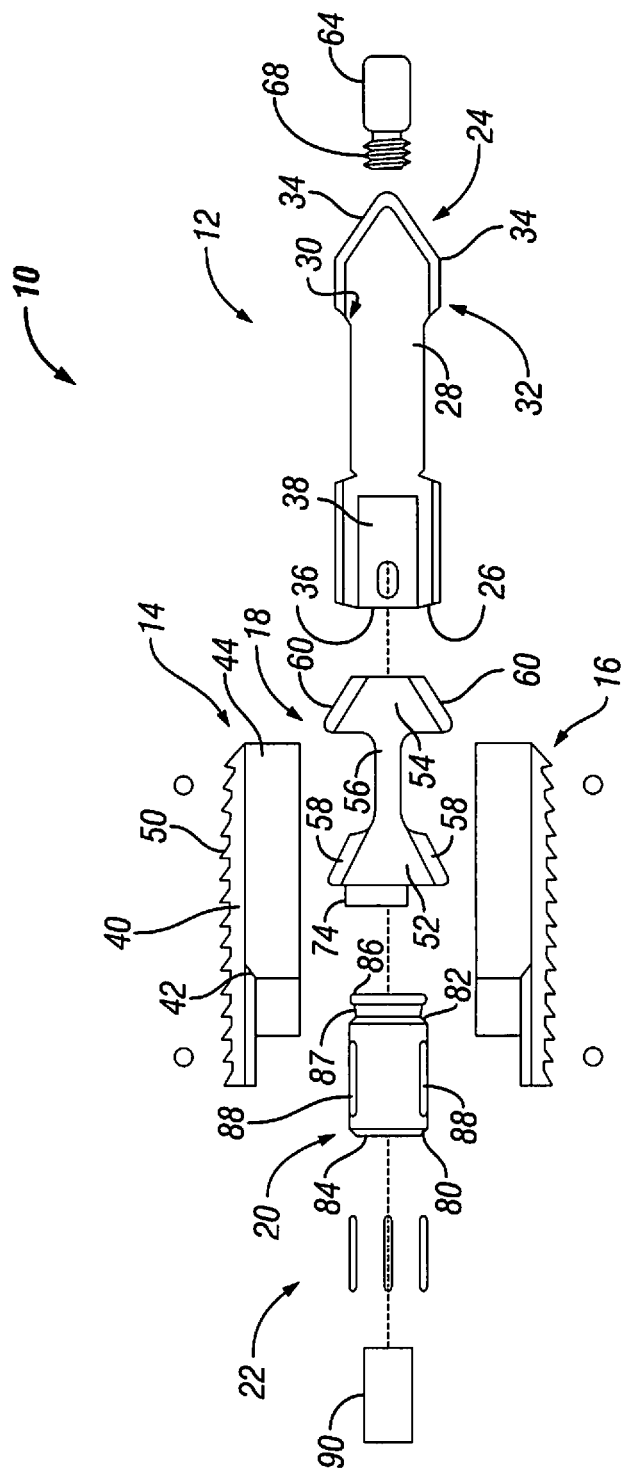
FIG. 2 is an exploded view of the expandable fusion device of FIG. 1.

With reference to FIG. 2, an exploded perspective view of one embodiment of the fusion device 10 is shown. In an exemplary embodiment, the fusion device 10 includes a body portion 12, a first endplate 14, a second endplate 16, a translation member 18, an actuation member 20, and an insert 22.

With additional reference to FIGS. 3-6, in an exemplary embodiment, the body portion 12 has a first end 24, a second end 26, a first side portion 28 connecting the first end 24 and the second end 26, and a second side portion 29 on the opposing side of the body portion 12 connecting the first end 24 and the second end 26. The body portion 12 further includes an upper end 30, which is sized to receive at least a portion of the first endplate 14, and a lower end 32, which is sized to receive at least a portion of the second endplate 16.

The first end 24 of the body portion 12, in an exemplary embodiment, includes at least one angled surface 34, but can include multiple angled surfaces. The angled surface 34 can serve to distract the adjacent vertebral bodies when the fusion device 10 is inserted into an intervertebral space. In another preferred embodiment, it is contemplated that there are at least two opposing angled surfaces forming a generally wedge shaped to distract the adjacent vertebral bodies when the fusion device 10 is inserted into an intervertebral space.

The second end 26 of the body portion 12, in an exemplary embodiment, includes an opening 36 which may include threading. In another exemplary embodiment, the opening 36 may include ratchet teeth instead of threading. The opening 36 extends from the second end 26 of the body portion 12 into a central opening (not illustrated) in the body portion 12. In one embodiment, the central opening is sized to receive the translation member 18, and the opening 36 is sized to threadingly receive the actuation member 20. In another exemplary embodiment, the opening 36 is sized to receive the actuation member 20 in a ratcheting fashion. In yet another exemplary embodiment, first side portion 28 and second side portion 29 each include a recess 38 located towards the second end 26 of the body portion 12. The recess 38 is configured and dimensioned to receive an insertion instrument (not shown) that assists in the insertion of the fusion device 10 into an intervertebral space.

Although the following discussion relates to the first endplate 14, it should be understood that it also equally applies to the second endplate 16 as the second endplate 16 is substantially identical to the first endplate 14 in embodiments of the present invention. Turning now to FIGS. 2-6, in an exemplary embodiment, the first endplate 14 has an upper surface 40, a lower surface 42, and a through opening 43. The through opening 43, in an exemplary embodiment, is sized to receive bone graft or similar bone growth inducing material and further allow the bone graft or similar bone growth inducing material to be packed in the central opening in the body portion 12.

Figure 3:
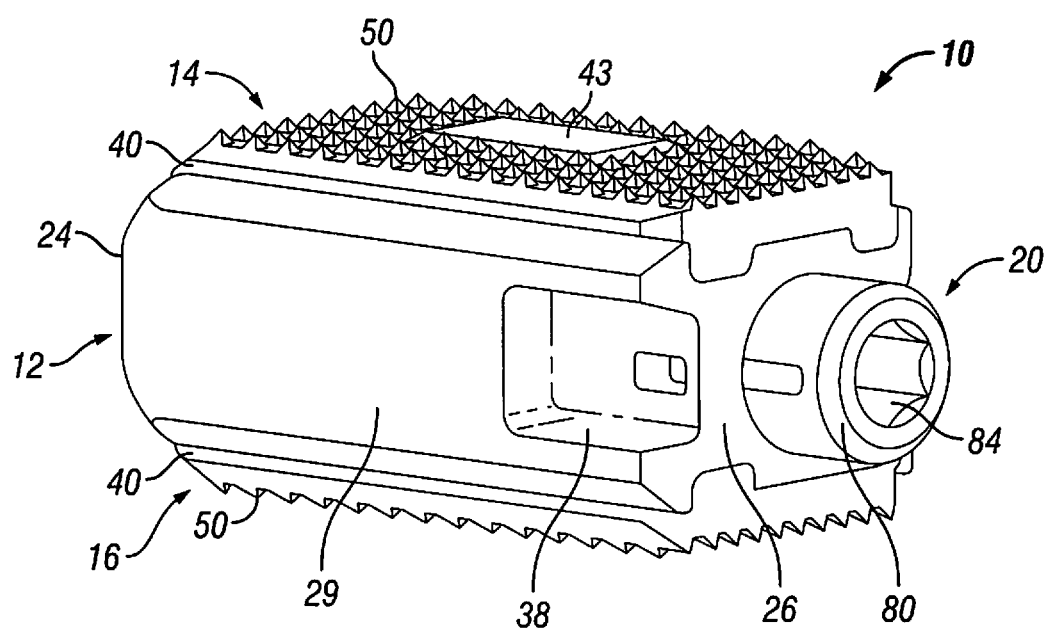
FIG. 3 is a rear perspective view of the expandable fusion device of FIG. 1 shown in an unexpanded position.
Figure 4:
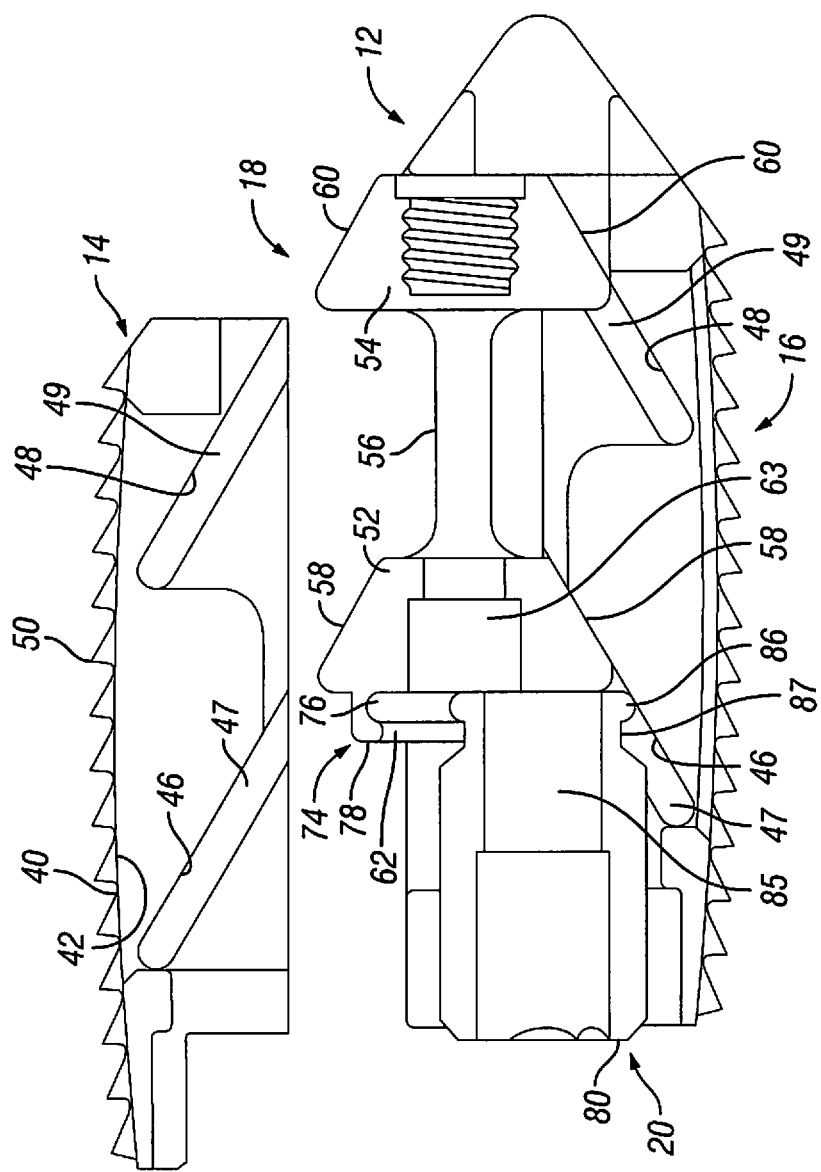
FIG. 4 is a side cross-sectional view of the expandable fusion device of FIG. 1 shown with one of the endplates removed.

In one embodiment, the lower surface 42 includes at least one extension 44 extending along at least a portion of the lower surface 42. As best seen in FIGS. 3 and 4, in an exemplary embodiment, the extension 44 can extend along a substantial portion of the lower surface 42, including, along each side of the endplate 14 and along the front end of the endplate 14. In another exemplary embodiment, the extension 44 includes at least one ramped portion 46, but can include any number of ramped portions, including two spaced ramped portions 46, 48 in the extension 44 that extend between each side of the endplate 14, as best seen in FIG. 4. It is contemplated that the slope of the ramped portions 46, 48 can be equal or can differ from each other. The effect of varying the slopes of the ramped portions 46, 48 is discussed below.

In an exemplary embodiment, the ramped portions 46, 48 further include grooved portions 47, 49 that are configured and dimensioned to receive angled surfaces 58, 60 of the translation member 18 and are oriented in an oblique fashion. In a preferred embodiment, the grooved portions 46, 48 are dovetail grooves configured and dimensioned to hold the angled surfaces 58, 60 of the translation member 18 while allowing the angles surfaces 58, 60 to slide against the ramped portions 46, 48.

Referring now to FIGS. 3-6, in one embodiment, the upper surface 40 of the first endplate 14 is flat and generally planar to allow the upper surface 40 of the endplate 14 to engage with the adjacent vertebral body 2. Alternatively, as shown in FIG. 7, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. Turning back to FIGS. 2-6, in an exemplary embodiment, the upper surface 40 includes texturing 50 to aid in gripping the adjacent vertebral bodies. Although not limited to the following, the texturing can include teeth, ridges, friction increasing elements, keels, or gripping or purchasing projections.

Figure 5:
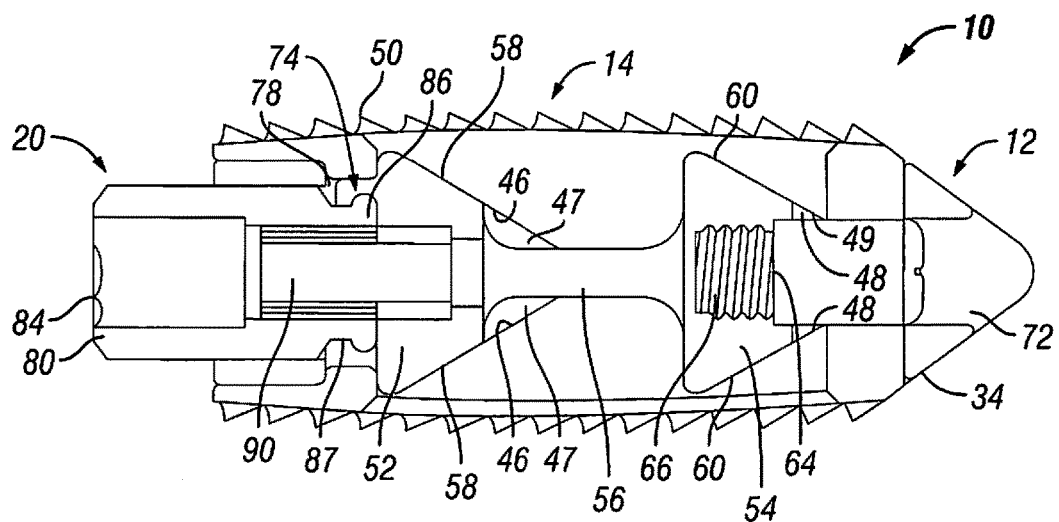
FIG. 5 is a side partial cross-sectional view of the expandable fusion device of FIG. 1 shown in an unexpanded position.
Figure 6:
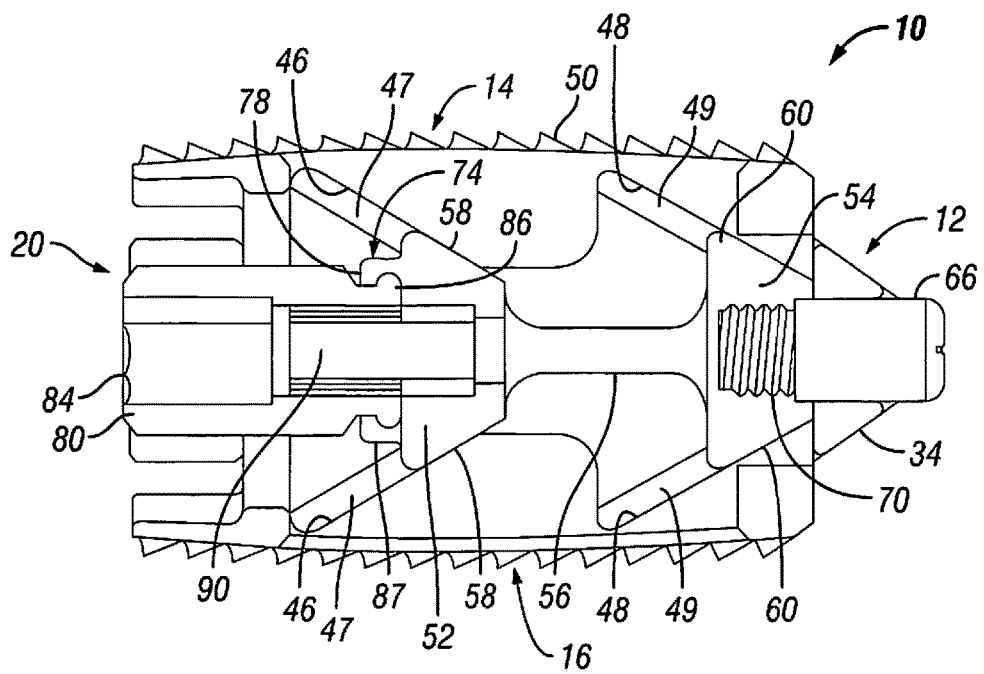
FIG. 6 is a side partial cross-sectional view of the expandable fusion device of FIG. 1 shown in an expanded position.
Figure 7:
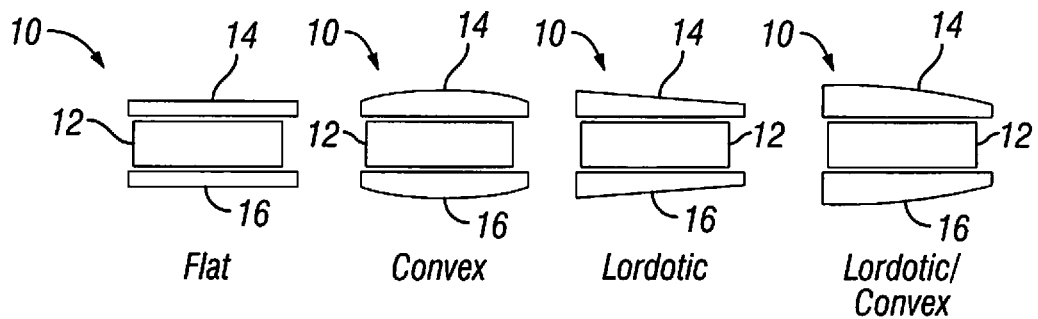
FIG. 7 is a side schematic view of the expandable fusion device of FIG. 1 having different endplates.

With reference to FIGS. 2 and 4-6, in an exemplary embodiment, the translation member 18 is sized to be received within the central opening of the body portion 12 and includes at least a first expansion portion 52. In another embodiment, the translation member 18 includes a first expansion portion 52 and a second expansion portion 54, the expansion portions 52, 54 being connected together via a bridge portion 56. It is also contemplated that there may be more than two expansion portions where each of the expansion portions is connected by a bridge portion. The expansion portions 52, 54 each have angled surfaces 58, 60 configured and dimensioned to engage the grooved portions 46, 48 of the first and second endplates 14, 16. In one embodiment, the translation member 18 includes an opening 62 in the first expansion portion 52, which is sized to receive a portion of the actuation member 20, as best seen in FIG. 4. In an exemplary embodiment, the first expansion portion 52 includes a central bore 63 that extends from the opening 62 and through the first expansion portion 52. In one embodiment, the translation member 18 includes a hole 64 in the second expansion portion 54, which is sized to receive nose 66, as best seen in FIGS. 5 and 6. In an exemplary embodiment, the hole 64 includes threading 68 for threadedly receiving a threaded end 70 of the nose 66, as shown on FIG. 6. The nose 66 is received in an opening 72 in the first end 34 of the body portion 12 to stabilize the translation member 18 in the central opening of the body portion 12.

In one embodiment, the translation member 18 includes a locking mechanism 74, which is configured and adapted to engage the actuation member 20. As illustrated, the locking mechanism 74 may extend from the first expansion portion 52. The locking mechanism 74 includes a slot 76 configured and adapted to receive extension 87 of the actuation member 20. In an exemplary embodiment, the locking mechanism 74 further includes a stop 78 (e.g., a rim, a lip, etc.) that engages the actuation member 20 when it is disposed in the slot 76.

Referring now to FIGS. 2-6, in an exemplary embodiment, the actuation member 20 has a first end 80, a second end 82, and threading (not illustrated) extending along at least a portion thereof from the first end 80 to the second end 82. The threading threadingly engages the threading that extends along a portion of opening 36 in the body portion 12. In another exemplary embodiment, the actuation member 20 includes ratchet teeth instead of threading. The ratchet teeth engage corresponding ratchet teeth in the opening 36 in the body portion 12. The first end 80 includes a recess 84 dimensioned to receive an instrument (not shown) that is capable of advancing the actuation member 20 with respect to the body portion 12 of the fusion device 10. In an embodiment, the actuation member 20 includes a bore 85, as best seen by FIG. 4, that extends from the recess 84 in the first end to the second 82. The second end 82 of the actuation member 20 includes an extension 86 that is received within the opening 62 in the first expansion portion 52. In one embodiment, the extension 88 may include a lip portion 86 and a plurality of slits 88. The plurality of slits 88 are configured to receive inserts 22. Inserts 22 are provided to limit motion of the actuation member 20. Once the lip portion 86 is placed into the slot 76 of the locking mechanism 74, the lip portion 86 will engage the stop 78 preventing longitudinal movement of the actuation member 20 with respect to the translation member 18. It is further contemplated that a pin member 90 can be included to further secure the actuation member 20 in the translation member 19. In an embodiment, the pin member 90 can be pressed into the central bore 85 of the actuation member 20 and the central bore 63 of the translation member, thereby preventing the actuation member 20 from disengaging from the translation member 18. Additionally, in an exemplary embodiment, the fusion device 10 can further include a chamfered tip 24 for distraction of adjacent vertebrae.

Turning now to FIGS. 1-6, a method of installing the expandable fusion device 10 is now discussed. Prior to insertion of the fusion device 10, the intervertebral space is prepared. In one method of installation, a diskectomy is performed where the intervertebral disc, in its entirety, is removed. Alternatively, only a portion of the intervertebral disc can be removed. The endplates of the adjacent vertebral bodies 2, 3 are then scraped to create an exposed end surface for facilitating bone growth across the invertebral space. The expandable fusion device 10 is then introduced into the intervertebral space, with the first end 22 of the body portion 12 being inserted first into the disc space followed by the second end 24. In an exemplary method, the fusion device 10 is in the unexpanded position when introduced into the intervertebral space. The wedged-shaped first end 22 should assist in distracting the adjacent vertebral bodies 2, 3, if necessary. This allows for the option of having little to no distraction of the intervertebral space prior to the insertion of the fusion device 10. In another exemplary method, the intervertebral space may be distracted prior to insertion of the fusion device 10. The distraction provide some benefits by providing greater access to the surgical site making removal of the intervertebral disc easier and making scraping of the endplates of the vertebral bodies 2, 3 easier.

Figure 1:
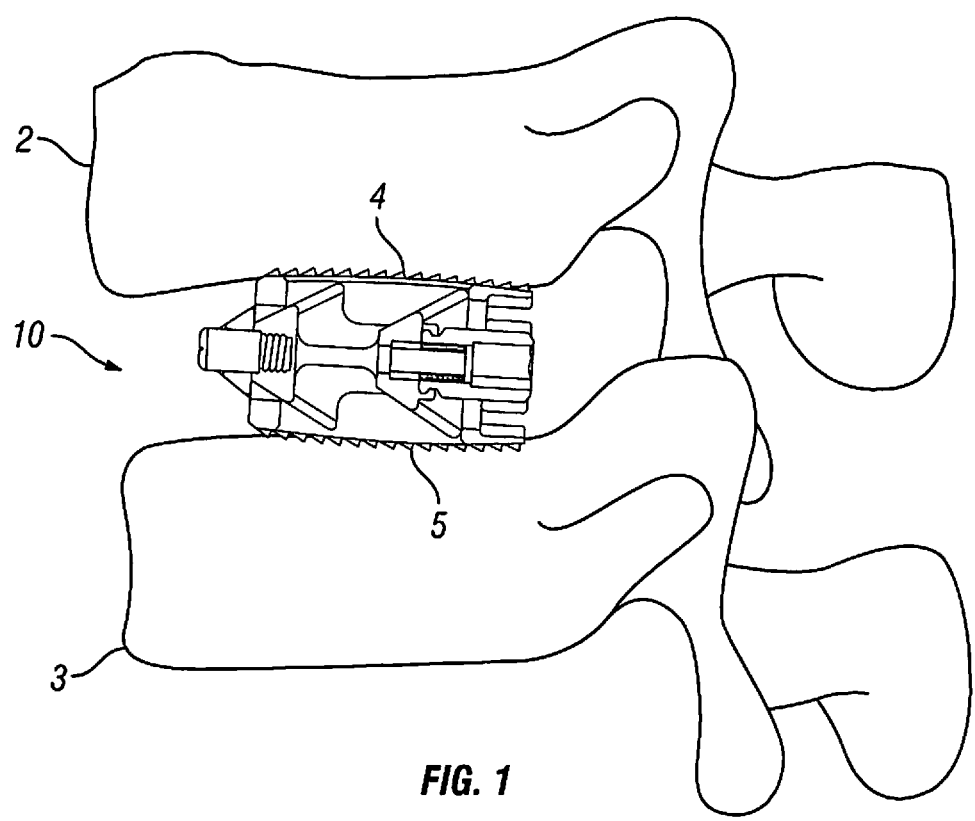
FIG. 1 is a side view of an embodiment of an expandable fusion device shown between adjacent vertebrae according to the present invention.

With the fusion device 10 inserted into and seated in the appropriate position in the intervertebral disc space, the fusion device can then expanded into the expanded position, as best seen in FIGS. 1, 5, and 6, To expand the fusion device 10, an instrument is engaged with recess 84 in the actuation member 20. The instrument is used to rotate actuation member 20. As discussed above, actuation member 20 can be threadingly engaging body portion 12 and is engaged with translation member 18; thus, as the actuation member 20 is rotated in a first direction, the actuation member 20 and the translation member 18 move with respect to the body portion 12 toward the first end 22 of the body portion 12. In another exemplary embodiment, the actuation member 20 is moved in a linear direction with the ratchet teeth engaging as means for controlling the movement of the actuation member 20 and the translation member 18. As the translation member 18 moves, the angled surfaces 58, 60 of the expansion portions 52, 54 push against the ramped portions 46, 48 of the endplates 14, 16 pushing endplates 14, 16 outwardly into the expanded position with the angled surfaces 58, 60 riding along the grooved portions 47, 48 of the ramped portions 46, 48. This can best be seen in FIGS. 5 and 6. Since the expansion of the fusion device 10 is actuated by a rotational input, the expansion of the fusion device 10 is infinite. In other words, the endplates 14, 16 can be expanded to an infinite number of heights dependent on the rotational advancement of the actuation member 20. As discussed above, the fusion device 10 includes a locking mechanism 22 which assists in retaining the endplates 14, 16 at the desired height.

Figure 8:
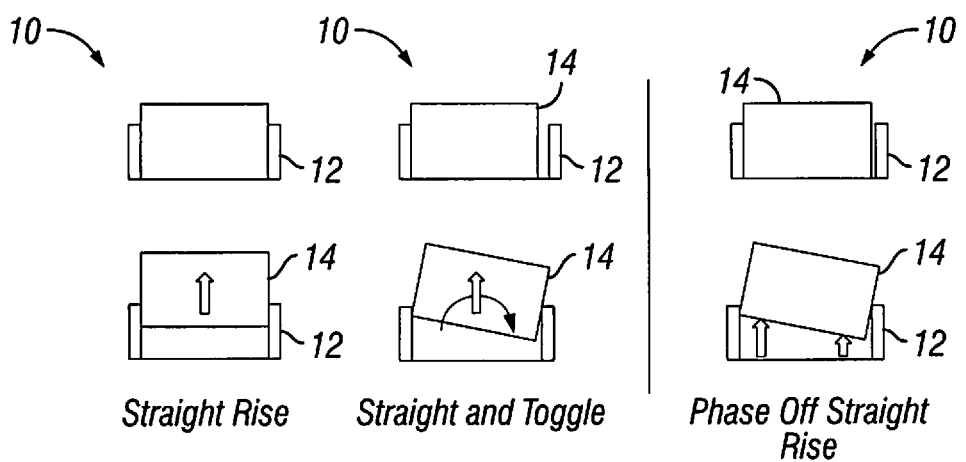
FIG. 8 is a partial side schematic view of the expandable fusion device of FIG. 1 showing different modes of endplate expansion.

It should also be noted that the expansion of the endplates 14, 16 can be varied based on the differences in the dimensions of the ramped portions 46, 48 and the angled surfaces 58, 60. As best seen in FIG. 8, the endplates 14, 16 can be expanded in any of the following ways: straight rise expansion, straight rise expansion followed by a toggle into a lordotic expanded configuration, or a phase off straight rise into a lordotic expanded configuration.

Turning back to FIGS. 1-6, in the event the fusion device 10 needs to be repositioned or revised after being installed and expanded, the fusion device 10 can be contracted back to the unexpanded configuration, repositioned, and expanded again once the desired positioning is achieved. To contract the fusion device 10, the instrument is engaged with recess 84 in the actuation member 20. The instrument is used to rotate actuation member 20. As discussed above, actuation member 20 can be threadingly engaging body portion 12 and is engaged with translation member 18; thus, as the actuation member 20 is rotated in a second direction, opposite the first direction, the actuation member 20 and translation member 18 move with respect to the body portion 12 toward the second end 26 of the body portion 12. As the translation member 18 moves, the angled surfaces 58, 60 of the translation member 18 ride along the grooved portions 47, 49 pulling the endplates 14, 16 inwardly into the unexpanded position.

Figure 9:
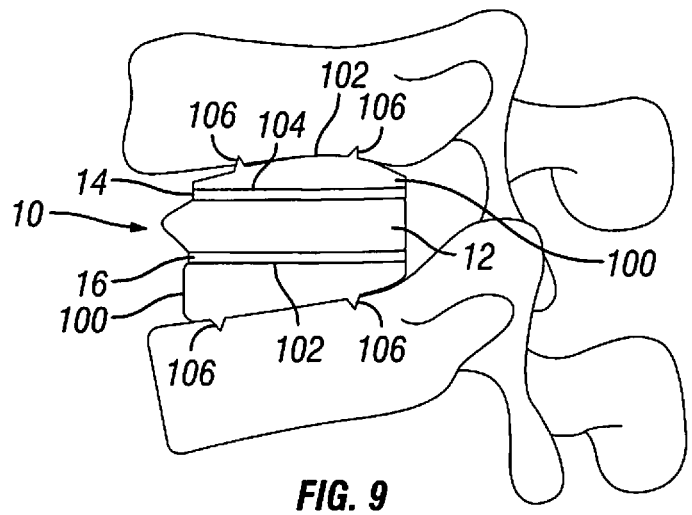
FIG. 9 is a side schematic view of the expandable fusion device of FIG. 1 with artificial endplates shown between adjacent vertebrae.

With reference now to FIG. 9, fusion device 10 is shown with an exemplary embodiment of artificial endplates 100. Artificial endplates 100 allows the introduction of lordosis even when the endplates 14 and 16 of the fusion device 10 are generally planar. In one embodiment, the artificial endplates 100 have an upper surface 102 and a lower surface 104. The upper surfaces 102 of the artificial endplates 100 have at least one spike 106 to engage the adjacent vertebral bodies. The lower surfaces 104 have complementary texturing or engagement features on their surfaces to engage with the texturing or engagement features on the upper endplate 14 and the lower endplate 16 of the fusion device 10. In an exemplary embodiment, the upper surface 102 of the artificial endplates 100 have a generally convex profile and the lower surfaces 104 have a generally parallel profile to achieve lordosis. In another exemplary embodiment, fusion device 10 can be used with only one artificial endplate 100 to introduce lordosis even when the endplates 14 and 16 of the fusion device 10 are generally planar. The artificial endplate 100 can either engage endplate 14 or engage endplate 16 and function in the same manner as described above with respect to two artificial endplates 100.

Figure 10:
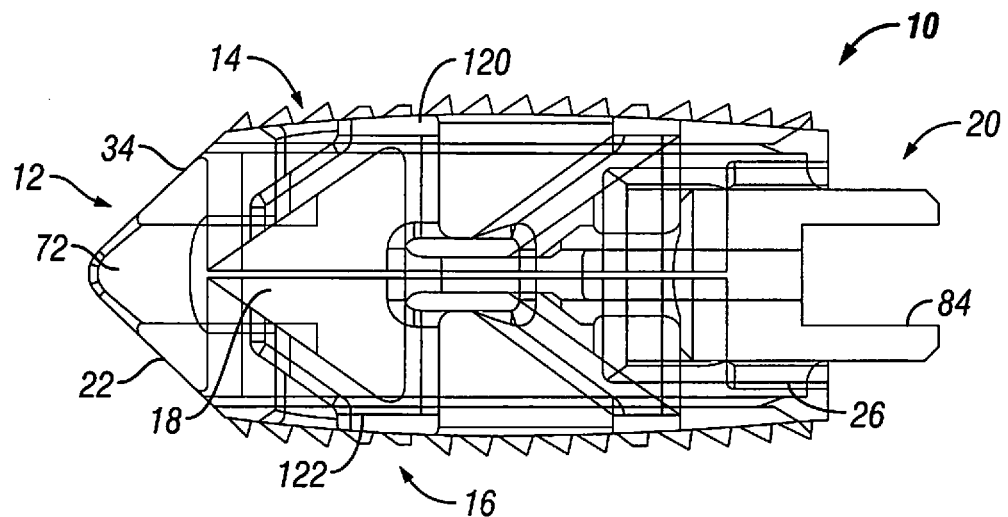
FIG. 10 is a side view cross-sectional view of another embodiment of an expandable fusion device shown in an unexpanded position.
Figure 11:
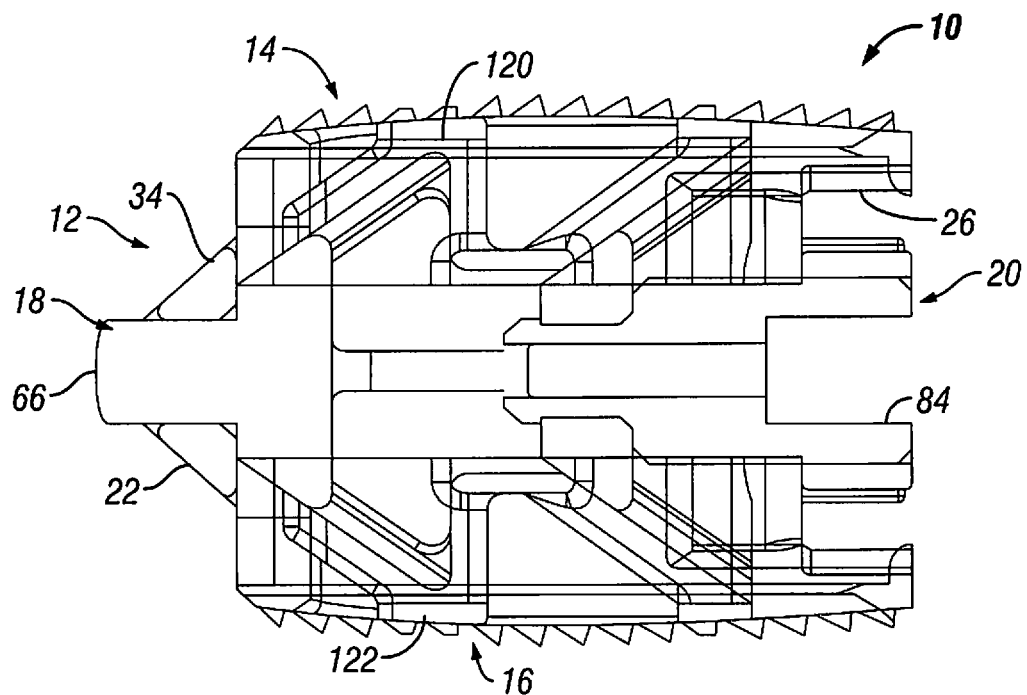
FIG. 11 is a side view cross-sectional view of the expandable fusion device of FIG. 10 shown in an expanded position.
Figure 12:
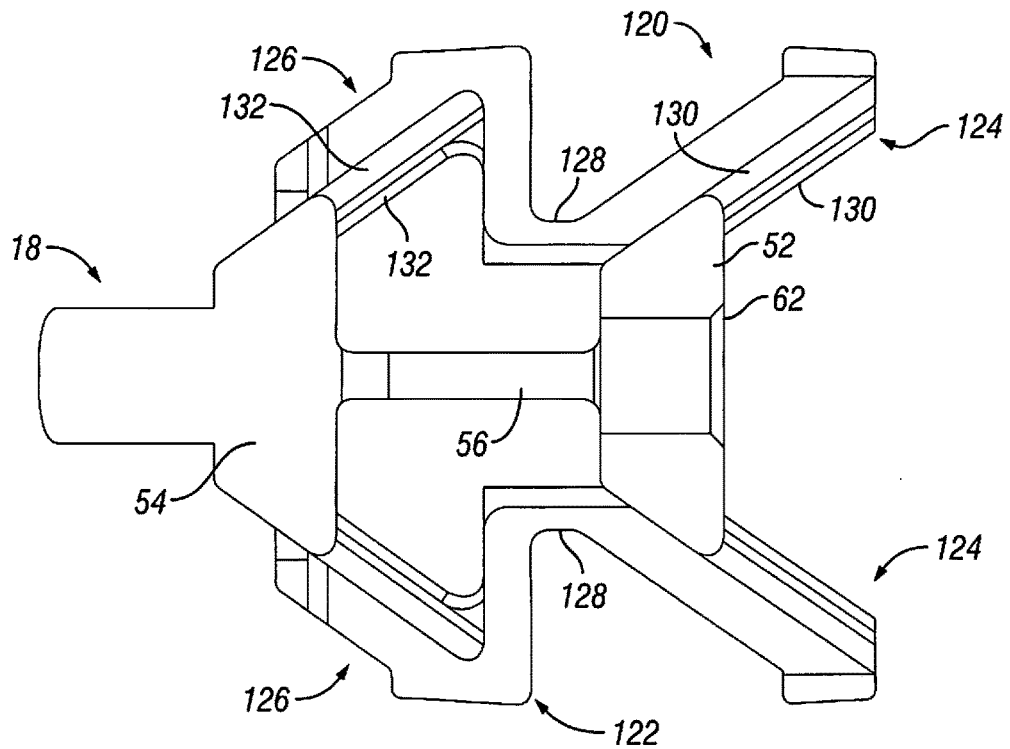
FIG. 12 is a side view of the expandable fusion device of FIG. 10 showing the translation member and the ramped insert.

Referring now to FIGS. 10 and 11, an alternative embodiment of the fusion device 10 is shown. In an exemplary embodiment, the fusion device 10 includes a body portion 12, a first endplate 14, a second endplate 16, a translation member 18, and an actuation member 20. In the illustrated embodiment, the fusion device further includes a first ramped insert 120 and a second ramped insert 122.

Although the following discussion relates to the first ramped insert 120, it should be understood that it also equally applies to the second ramped insert 122 as the second ramped insert 122 is substantially identical to the first ramped insert 120 in embodiments of the present invention. Turning now to FIGS. 10-13, in an exemplary embodiment, the first ramped insert 120 includes a first ramped portion 124 and a second ramped portion 126, the first and second ramped portions 124, 126 being connected by a bridge portion 128. The ramped portions 124, 126 each have grooved portions 130, 132 configured and dimensioned to receive angled surfaces 58, 60 of the translation member. The ramped portions 124, 126 can be oriented in an oblique fashion, as illustrated. In a preferred embodiment, the grooved portions 130, 132 are dovetail grooves configured and dimensioned to hold the angled surfaces 58, 60 of the translation member 18 while allowing the angles surfaces 58, 60 to slide against the ramped portions 124, 126.

In an exemplary embodiment, the first ramped insert 120 should be configured and dimensioned to be engaged with the first endplate 14. In an embodiment, the first and second ramped portions 124, 126 include snap connectors 134, 136 for securing the first ramped insert 120 to the first endplate. It should be understood that the snap connectors 134, 136 are merely illustrative and that other suitable mechanisms for securing the first ramped inserted 120 with the first endplate 14 may be used.

Figure 13:
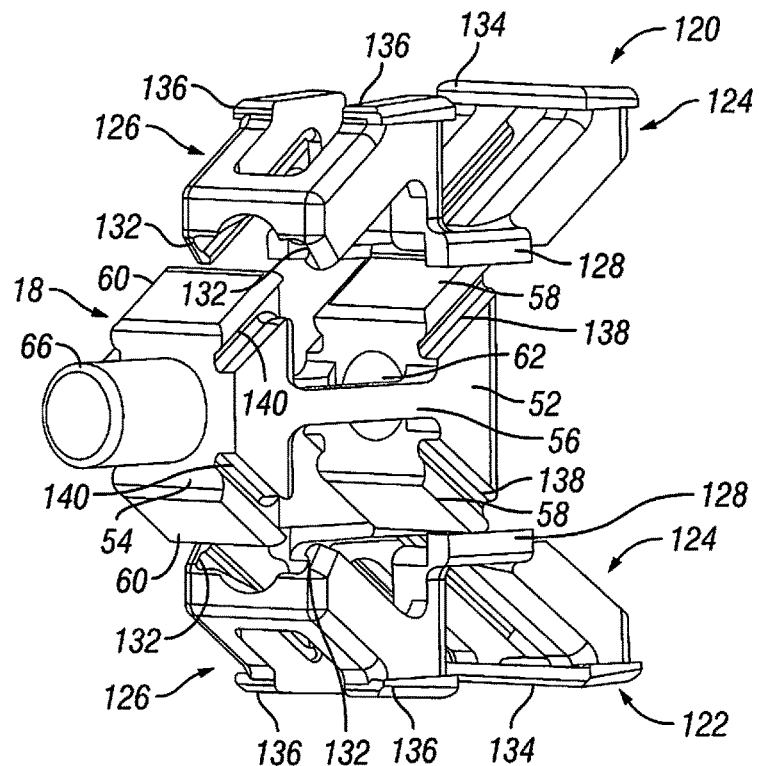
FIG. 13 is a front perspective view of the expandable fusion device of FIG. 10 showing the translation member and the ramped insert.

Referring to FIGS. 10-13, in an exemplary embodiment, the translation member 18 is sized to be received within the central opening of the body portion 12 and includes at least a first expansion portion 52. In another embodiment, the translation member 18 includes a first expansion portion 52 and a second expansion portion 54, the expansion portions 52, 54 being connected together via a bridge portion 56. It is also contemplated that there may be more than two expansion portions where each of the expansion portions is connected by a bridge portion. The expansion portions 52, 54 each have angled surfaces 58, 60 configured and dimensioned to engage the grooved portions 130, 132 of the first and second ramped inserts 120, 122. In one embodiment, the angled surfaces 58, 60 include corresponding grooved portions 138, 140, as best seen in FIG. 13, that slidingly engaged the grooved portions 130, 132 of the first and second ramped inserts 120, 122.

In one embodiment, the expansion portion 52 includes an opening 62, which is sized to receive a portion of the actuation member 20, and the expansion portion 62 includes a nose 66, which is received within an opening 72 in the first end 34 of the body portion 12 to stabilize the translation member 18 in the central opening of the body portion 12. In an embodiment, the nose 66 is integral with the expansion portion 62. In an embodiment (shown on FIGS. 2 and 4-6), the nose 66 is threadingly engaged with the expansion portion 62. In an embodiment, the translation member 18 includes a locking mechanism 74 to engage the actuation member 20, as illustrated in FIGS. 2-6. However, it should be understood that other suitable mechanisms may be used to secure the actuation member 20 within the translation member 18. For example, the actuation member 20 may include an extension 87 having a lip portion 86 (shown on FIGS. 2 and 4-6) that engages the expansion portion 62. The extension 87 may, for example, be configured to flex inwardly reducing its diameter when received in the opening 62. Once the lip portion 86 of the extension 87 is advanced beyond the end of the opening 62, the extension portion 87 will return back to its original diameter and the lip portion 86 will engage the expansion portion 60.

The expandable fusion device 10 of FIGS. 10-13 can be inserted into the intervertebral space in a manner similar to that the previously described with respect to FIGS. 1-6. After insertion, the expandable fusion device 10 of FIGS. 10-13 can be expanded into the expanded position, as best seen in FIGS. 10 and 11. To expand the fusion device 10, an instrument is engaged with recess 84 in the actuation member 20. The instrument is used to rotate actuation member 20. As discussed above, actuation member 20 can be threadingly engaging body portion 12 and is engaged with translation member 18; thus, as the actuation member 20 is rotated in a first direction, the actuation member 20 and the translation member 18 move with respect to the body portion 12 toward the first end 22 of the body portion 12. In another exemplary embodiment, the actuation member 20 is moved in a linear direction with the ratchet teeth engaging as means for controlling the movement of the actuation member 20 and the translation member 18. As the translation member 18 moves, the angled surfaces 58, 60 of the expansion portions 52, 54 push against the ramped portions 124, 126 of the first and second ramped inserts 120, 122 while riding along the grooved portions 130, 132, thus pushing first and second ramped inserts 120, 122 outwardly. Because the first and second ramped inserts 120, 122 are engaged with the endplates 14, 16, the endplates 14, 16 are also pushed outwardly into the expanded position.

After expansion, the expandable fusion device 10 can be contracted back to the unexpanded configuration. To contract the fusion device 10, the instrument is engaged with recess 84 in the actuation member 20. The instrument is used to rotate actuation member 20. As discussed above, actuation member 20 can be threadingly engaging body portion 12 and is engaged with translation member 18; thus, as the actuation member 20 is rotated in a second direction, opposite the first direction, the actuation member 20 and translation member 18 move with respect to the body portion 12 toward the second end 26 of the body portion 12. As the translation member 18 moves, the angled surfaces 58, 60 of the translation member 18 ride along the grooved portions 130, 132 pulling the first and second ramped inserts 120, 122 and thus, the endplates 14, 16 inwardly into the unexpanded position.

Figure 14:
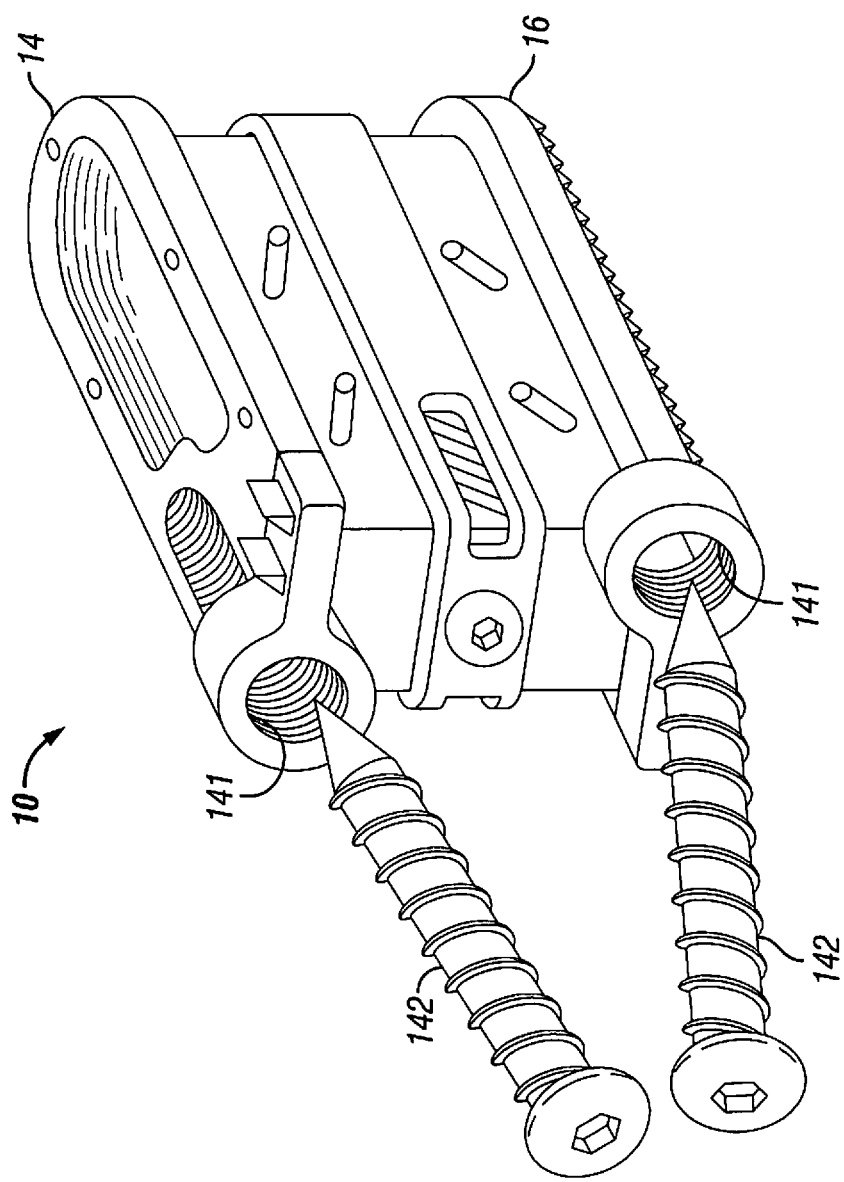
FIG. 14 is a rear perspective of another embodiment of an expandable fusion device with the endplates having a threaded hole.

Referring now to FIG. 14, an alternative embodiment of the fusion device 10 is shown. In an exemplary embodiment, the first endplate 14 and the second endplate 16 each include additional geometry to help securely hold the endplates 14, 16 in place. In an embodiment, the first endplate 14 and/or the second endplate 16 include threaded holes 141 through which the fasteners, such as screws 142, may be inserted. In an embodiment, the threaded holes 141 penetrate through the first endplate 14 and/or the second endplate 16 in an oblique fashion. It is contemplated that the screws 142 may inserted through the threaded holes 141 and into adjacent vertebral bodies 2, 3, to further secure the first endplate 14 and the second endplate 16 to the vertebral bodies 2, 3. In some embodiments, these fasteners may be removed once a more long-term interface has been established, or alternatively the fasteners may remain in place indefinitely or until the fusion device 10 needs adjustment and/or replacement.

Figure 15:
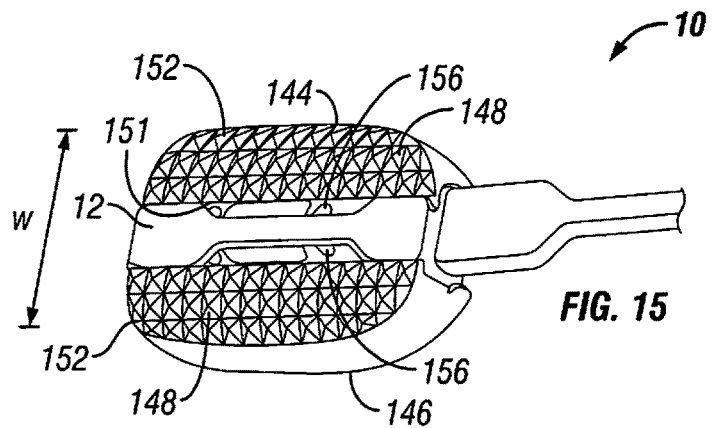
FIG. 15 is a top view of another embodiment of an expandable fusion device shown in an unexpanded position.
Figure 16:
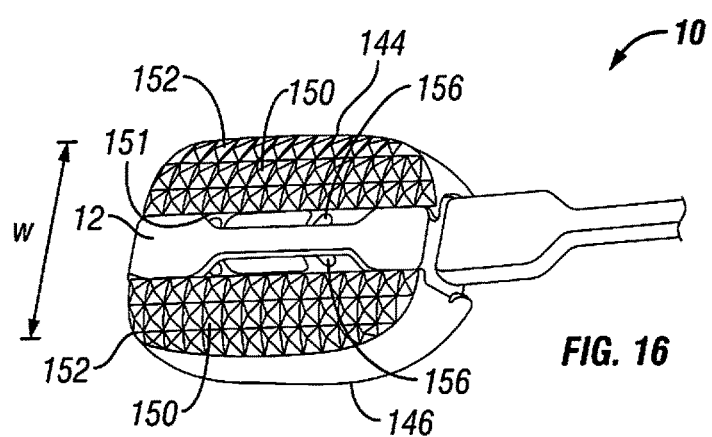
FIG. 16 is a bottom view of the expandable fusion device of FIG. 15.
Figure 17:
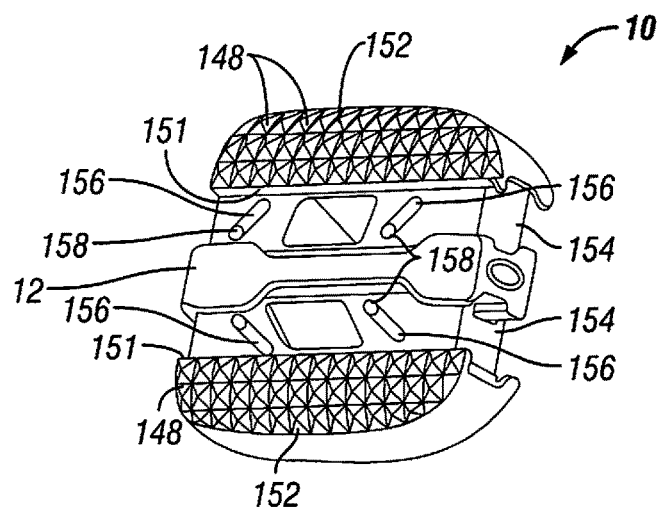
FIG. 17 is top view of the expandable fusion device of FIG. 15 shown in an expanded position.

With reference now FIGS. 15-17, an alternative embodiment of the fusion device 10 is shown that expands laterally. Lateral expansion maximizes coverage of the intravertebral disc space for wider load distribution and stability providing a rigid foundation for fusion. In one embodiment, the fusion device 10 includes body portion 12, first endplate 144, and second endplate 146.

Although the following discussion relates to the first endplate 144, it should be understood that it also equally applies to the second endplate 146 as the second endplate 146 is substantially identical to the first endplate 144 in embodiments of the present invention. Turning now to FIGS. 15-17, in an exemplary embodiment, the first endplate 144 has an upper surface 148, a lower surface 150, and an inner surface 151 facing the body portion 12. It is contemplated that the upper surface 148 will engage adjacent vertebral body 2 (seen on FIG. 1) and the lower surface 150 will engage adjacent vertebral body 3 (seen on FIG. 1). In one embodiment, the upper surface 148 and the lower surface 150 are each flat and generally planar to allow the upper surface 148 to engage with the adjacent vertebral body 3. Alternatively, the upper surface 148 and/or the lower surface 150 can be curved convexly or concavely to allow for a greater or lesser degree of engagement with the adjacent vertebral bodies 2, 3. It is also contemplated that the upper surface 148 and/or the lower surface 150 can be generally planar but includes a generally straight ramped surface or a curved ramped surface. The ramped surface allows for engagement with the adjacent vertebral body 2 and/or the adjacent vertebral body 3 in a lordotic fashion. In an exemplary embodiment, the upper surface 148 and/or lower surface 150 includes textures 152 to aid in gripping the adjacent vertebral bodies. Although not limited to the following, the texturing can include teeth, ridges, friction increasing elements, keels, or gripping or purchasing projections.

In one embodiment, the inner surface 151 includes at least one extension 154 extending along at least a portion of the inner surface 151. In an exemplary embodiment, the extension 154 can extend along a substantial portion of the inner surface 154, including, along each side of the endplate 144 and along the front end of the endplate 14. While not illustrated, the inner surface may include ramped surfaces and grooved portions in an exemplary embodiment. It is contemplated that the ramped surfaces and/or grooved portions may be similar to the ramped surfaces 46, 48 and grooved portion 47, 49 in extension 44 shown on FIGS. 4-6. In an embodiment, the extension 154 may include slots 156 oriented in an oblique fashion through which pins 158 may be inserted.

While not illustrated, the fusion device 10 further includes features to effectuate the lateral expansion of the first and second endplates 144, 146. In one embodiment, the fusion device 10 using a ramping system—similar to the system illustrated in FIGS. 2 and 4-6—for expanding the first and second endplates 144, 146. In an exemplary embodiment, the fusion device 10 further includes a translation member and actuation member, such as translation member 18 and actuation member 20 shown on FIGS. 2 and 4-6. It is contemplated that the translation member may include angled surfaces that push against ramped surfaces in the extension 154, expanding the first and second endplates 144, 146 outwardly and away from the body portion 12. In an embodiment, pins 156 disposed through the slots 154 may be retained in the translation member. In an alternative embodiment, dovetailing may be used for engagement of the angled surfaces and ramped surfaces. It should be understood that the translation member and actuation member in this embodiment may be similar to the translation member 18 and actuation member 20 described above with respect FIGS. 1-6. In another embodiment, the fusion device 10 further includes first and second ramped inserts that are secured within the first and second endplates 144, 146. The first and second ramped inserts may be similar to the first and second ramped inserts 120, 122 described above with respect to FIGS. 10-13. It is contemplated that angled surfaces in the translation member may push against ramped surfaces in the ramped inserts pushing the ramped inserts outwardly. Because of their engagement with the first and second endplates 144, 146, the first and second endplates 144, 146 may thus be expanded outwardly. In this manner, the first and second endplates 144, 146 may be laterally expanded away from the body portion 12. It should be understood that other suitable techniques may also be used to effectuate this lateral expansion.

Figure 18:
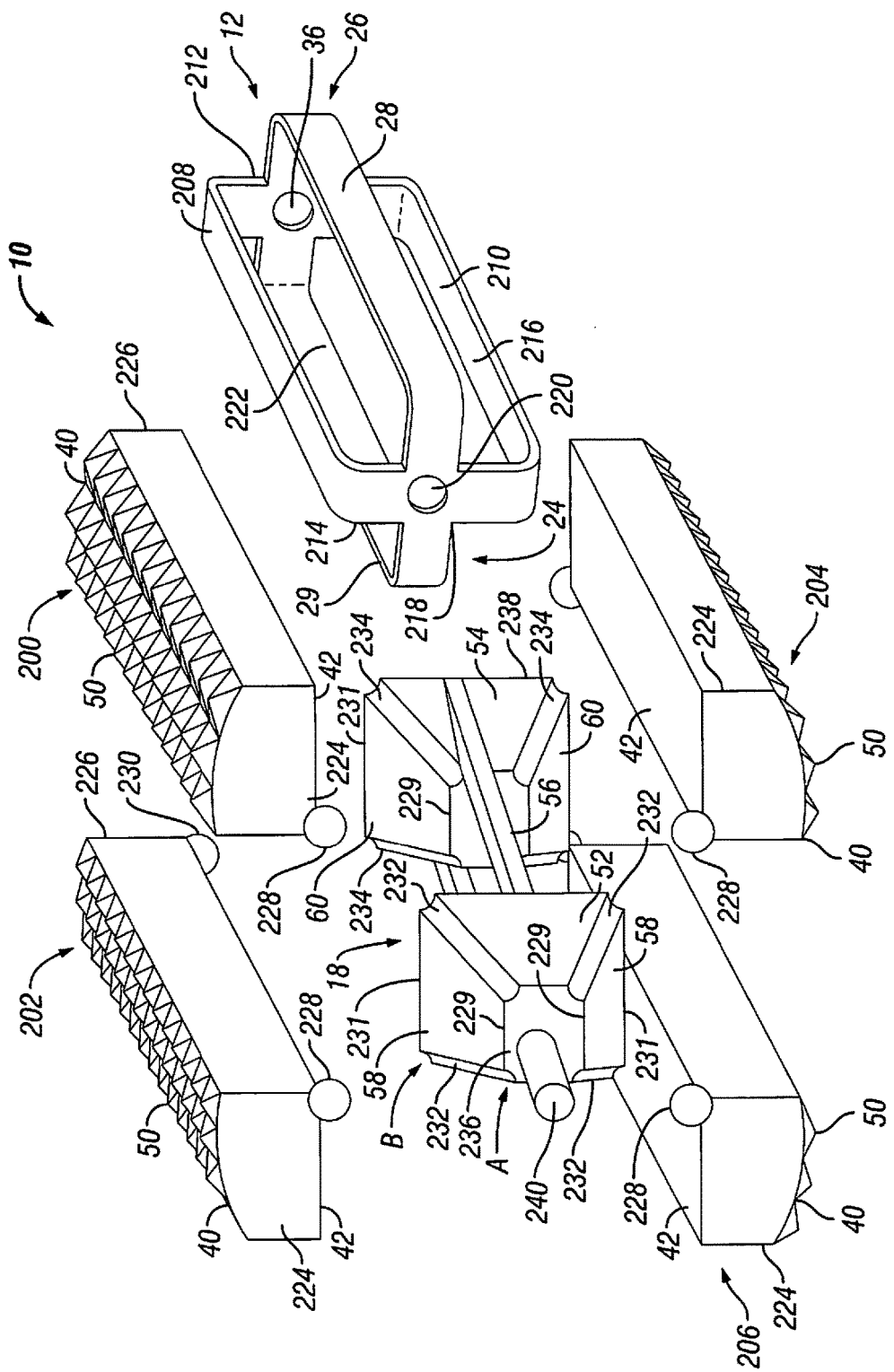
FIG. 18 is an exploded perspective view of another embodiment of an expandable fusion device.

With reference to FIG. 18, an exploded perspective view of another embodiment of fusion device 10 is shown. In an exemplary embodiment, the fusion device 10 includes a body portion 12, a first endplate 200, a second endplate 202, a third endplate 204, a fourth endplate 206, and a translation member 18. In this embodiment, the fusion device 10 is configured to expand both vertically and laterally.

In an exemplary embodiment, the body portion 12 has a first end 24, a second end 26, a first side portion 28 connecting the first end 24 and the second end 26, and a second side portion 29 on the opposing side of the body portion 12 connecting the first end 24 and the second end 26. The body portion 12 further includes a top side portion 208 connecting the first end 24 and the second end 26, and a bottom side portion 210 on the opposing side of the body portion 12 connecting the first end 24 and the second end 26. The body portion 12 further includes first gap 212 between the top side portion 208 and the first side portion 28, which is sized to receive at least a portion of the first endplate 200. The body portion 12 further includes second gap 214 between the top side portion 208 and the second side portion 29, which is sized to receive at least a portion of the second endplate 202. The body portion 12 further includes third gap 216 between the bottom side portion 210 and the first side portion 28, which is sized to receive at least a portion of the third endplate 204. The body portion 12 further includes fourth gap 218 between the bottom side portion 210 and the second side portion 29, which is sized to receive at least a portion of the fourth endplate 206.

The first end 24 of the body portion 12, in an exemplary embodiment, includes an opening 220. The opening 220 extends from the first end 24 of the body portion 12 into a central opening 222. In one embodiment, the central opening 222 is sized to receive the translation member 18. The second end 26 of the body portion 12, in an exemplary embodiment, includes an opening 36, which extends from the second end 26 of the body portion 12 into the central opening 222.

Figure 19:
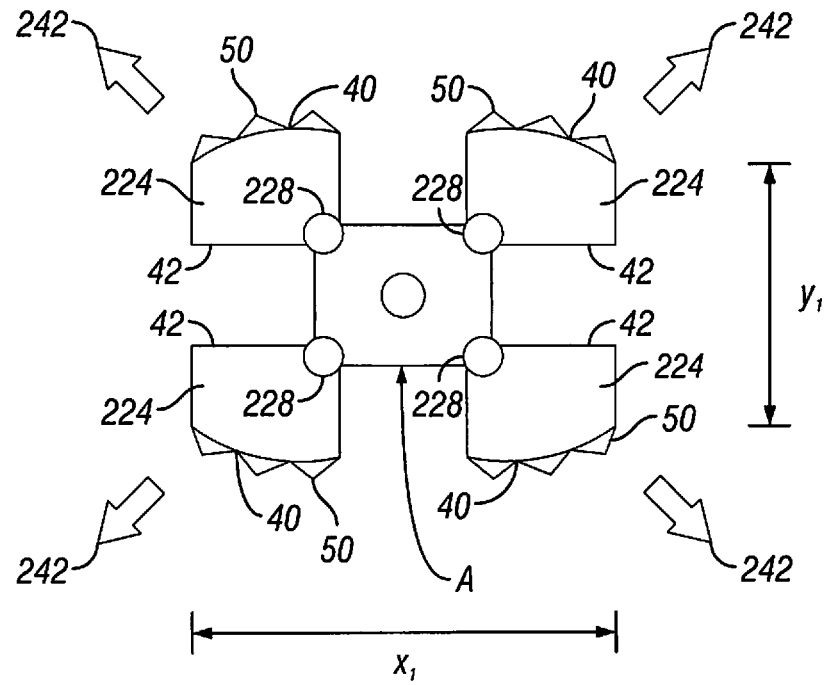
FIG. 19 is an end view of the expandable fusion device of FIG. 18 in an unexpanded position.
Figure 20:
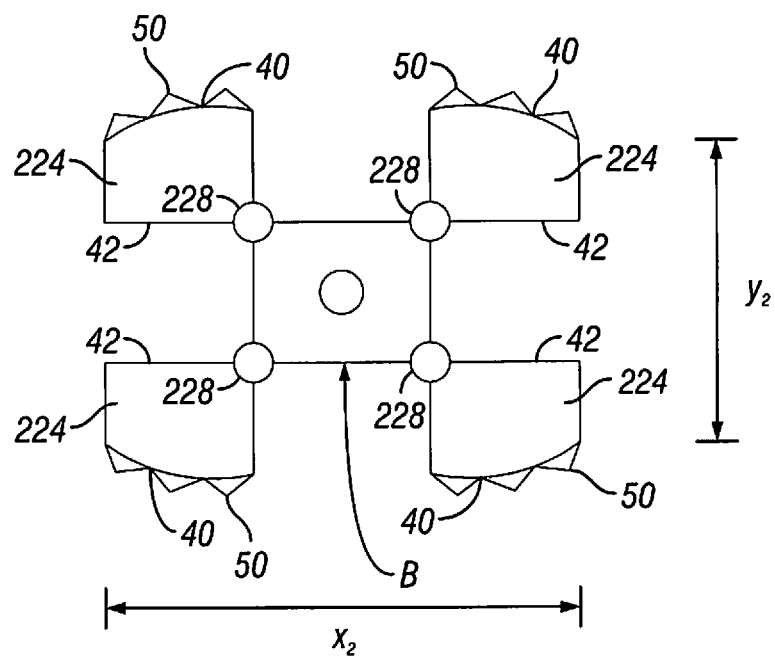
FIG. 20 is an end view of the expandable fusion device of FIG. 18 in an expanded position.

Although the following discussion relates to the first endplate 200, it should be understood that it also equally applies to the second endplate 202, the third endplate 204, and the fourth endplate 206, as these endplates 202, 204, 206 are substantially identical to the first endplate 200 in embodiments of the present invention. Turning now to FIGS. 18-20, in an exemplary embodiment, the first endplate 14 has a first end 224 and a second end 226. The first endplate further includes an upper surface 40 connecting the first end 224 and the second end 226 and a lower surface 42 on an opposing side of the endplate 200 connecting the first end 224 and the second end 226. While not illustrated, the first endplate 14 may include a through opening sized to receive bone graft or similar bone growth inducing material and further allow the bone graft or similar bone growth inducing material to be packed in the central opening 222 in the body portion 12.

In one embodiment, the lower surface 42 includes at least one first retaining socket 228 on the lower surface 42. In an exemplary embodiment, the lower surface 42 includes a first retaining socket 228 at the interior corner of the intersection of the first end 224 and the lower surface 42, and a second retaining socket 230 at the interior corner of the intersection of the first end 224 and the lower surface 42.

Referring now to FIGS. 18-20, in one embodiment, the upper surface 40 of the first endplate 200 is curved convexly. Alternatively, the upper surface 40 is flat or curved concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. In an exemplary embodiment, the upper surface 40 includes texturing 50 to aid in gripping the adjacent vertebral bodies. Although not limited to the following, the texturing can include teeth, ridges, friction increasing elements, keels, or gripping or purchasing projections.

With reference to FIG. 18, in an exemplary embodiment, the translation member 18 is sized to be received within the central opening 222 of the body portion 12. The translation member 18 should be sized to allow longitudinal translation within the central opening 222. In an embodiment, the translation member 18 includes at least a first expansion portion 52. In another embodiment, the translation member 18 includes a first expansion portion 52 and a second expansion portion 54, the expansion portions 52, 54 being connected together via a bridge portion 56. It is also contemplated that there may be more than two expansion portions where each of the expansion portions is connected by a bridge portion. The expansion portions 52, 54 each have angled surfaces 58, 60. In an embodiment, the angles surfaces 58, 60 each comprise first end 229 and second end 231 with second end 231 being wider than the first end 229. In an exemplary embodiment, the expansion portions 52, 54 include grooved portions 232, 234 on the edges of at least two sides (e.g., the lateral sides) of the angled surfaces 58, 60. The grooved portions 232, 234 are configured and dimensioned to engage the first and second retaining sockets 228, 230 on the endplates 200, 202, 204, 206. In an exemplary embodiment, the grooved portions 232, 234 retain the first and second retaining sockets 228, 230 in sliding engagement.

In one embodiment, the translation member 18 includes a first end 236 and a second end 238. The first end 236 of the translation member includes an extension 240 sized to be received within the opening 220 in the first end 24 of the body portion 12. While not illustrated, the second end 238 also can include a similar extension sized to be received within opening 32 in the second end 26 of the body portion 12.

The expandable fusion device 10 of FIGS. 18-20 can be inserted into the intervertebral space in a manner similar to that the previously described with respect to FIGS. 1-6. After insertion, the expandable fusion device 10 of FIGS. 18-20 can be expanded into the expanded position. As previously mentioned, the fusion device 10 shown on FIGS. 18-20 expands both vertically and laterally. To expand the fusion device 10, the translation member 18 can be moved with respect to the body portion 12 toward the first end 24 of the body portion. An instrument can be used, in an exemplary embodiment. As the translation member 18 moves, the first retaining socket 228 and the second retaining socket 230 ride along the grooved portions 232, 234 of the expansion portions 52, 54 pushing the endplates 200, 202, 204, 206 outwardly in the direction indicated by arrows 242. In an embodiment, the endplates 200, 202, 204, 206 move outwardly in an oblique fashion to expand the fusion device 10 both vertically and laterally. The expanded configuration of the expansion device 10 is best seen in FIG. 20.

After expansion, the expandable fusion device 10 can be contracted back to the unexpanded configuration. The unexpanded configuration of the fusion device 10 is best seen in FIG. 20. To contract the fusion device 10, the translation member 18 is moved with respect to the body portion 12 toward the second end 26 of the body portion 12. As the translation member 18 moves, the first retaining socket 228 and the second retaining socket 230 ride along the grooved portions 232, 234 of the expansion portions 52, 54 pulling the endplates 200, 202, 204, 206 inwardly in a direction opposite that indicated by arrows 242. In an embodiment, the endplates 200, 202, 204, 206 move inwardly in an oblique fashion to contract the fusion device 10 both vertically and laterally. The unexpanded configuration of the expansion device 10 is best seen in FIG. 19.

Figure 21:
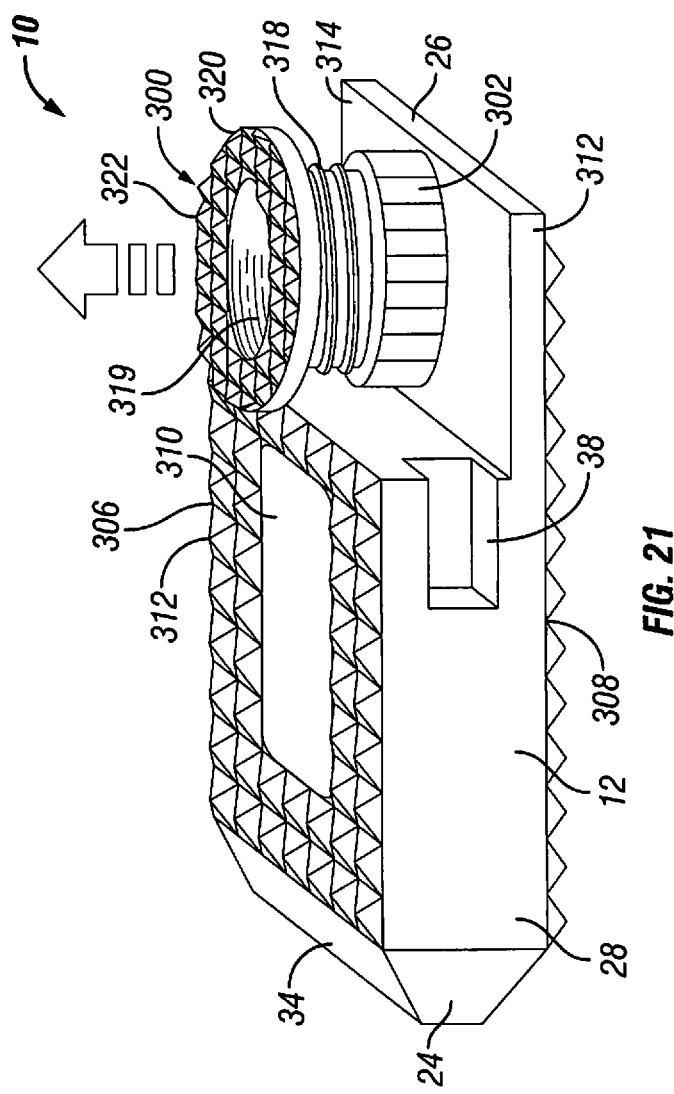
FIG. 21 is a perspective view of another embodiment of an expandable fusion device.
Figure 22:
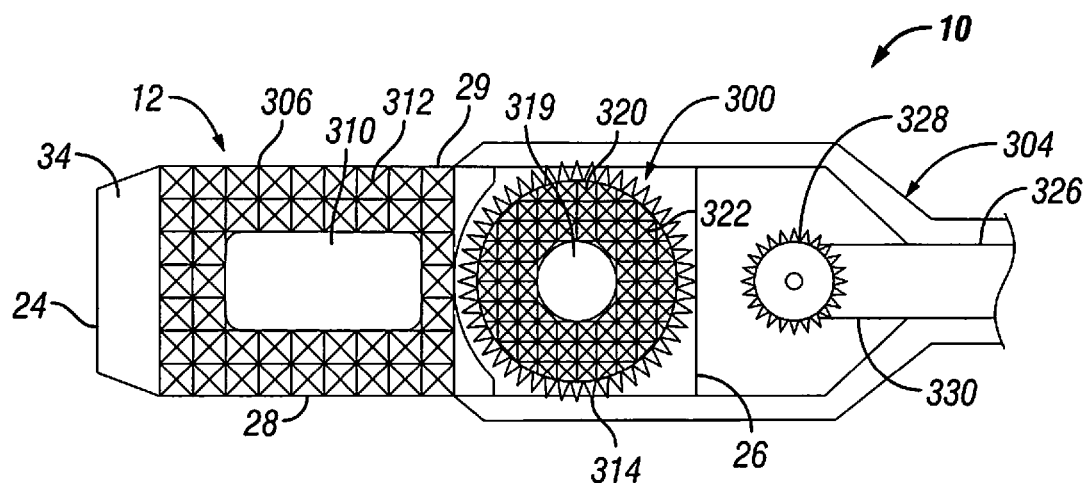
FIG. 22 is a top view of the expandable fusion device of FIG. 21.

With reference to FIGS. 21-22, another embodiment of expandable fusion device 10 is shown. In an exemplary embodiment, the fusion device 10 includes a body portion 12, a vertically expanding plate 300, and a gear 302. In this embodiment, a portion of the fusion device 10 is configured to expand vertically in at least one direction. In an exemplary embodiment, the vertically expanding plate 300 is configured to expand outwardly from the body portion 12. It is contemplated that an expandable fusion device 10 may be used to correct spinal curvature due to, for example, scoliosis, lordosis, and the like.

In an exemplary embodiment, the body portion 12 has a first end 24, a second end 26, a first side portion 28 connecting the first end 24 and the second end 26, and a second side portion 29 on the opposing side of the body portion 12 connecting the first end 24 and the second end 26. The first end 24 of the body portion 12, in an exemplary embodiment, includes at least one angled surface 34, but can include multiple angled surfaces. The angled surface 34 can serve to distract the adjacent vertebral bodies when the fusion device 10 is inserted into an intervertebral space. In another preferred embodiment, it is contemplated that there are at least two opposing angled surfaces forming a generally wedge shaped to distract the adjacent vertebral bodies when the fusion device 10 is inserted into an intervertebral space. In yet another preferred embodiment, first side portion 28 and second side portion 29 each include a recess 38 located towards the second end 26 of the body portion 12. The recess 38 is configured and dimensioned to receive an insertion instrument 304 that assists in the insertion of the fusion device 10 into an intervertebral space.

In an exemplary embodiment, the body portion 12 includes an upper engagement surface 306 extending from the first end 24 towards the second end 26, and a lower engagement surface 308 extending between the first end 24 and the second end 26. In an embodiment, the upper engagement surface 306 has a through opening 310. Although not illustrated, the lower engagement surface 308 may have a through opening that is similar to through opening 310. The through opening 310, in an exemplary embodiment, is sized to receive bone graft or similar bone growth inducing material and further allow the bone graft or similar bone growth inducing material to be packed in the central opening in the body portion 12. In an embodiment, at least a portion of the body portion 12 is removed to form a landing 312 in the body portion 12. In an exemplary embodiment, a portion of the upper engagement surface 306 and the second end 26 are removed to form the landing 312 having an upper surface 314. While not illustrated, a portion of the lower engagement surface 308 and the second end 26 may be cut away, in an alternative embodiment, to form the landing 312.

In one embodiment, the upper engagement surface 306 and the lower engagement surface 308 are flat and generally planar to allow engagement surfaces 306 to engage with the adjacent vertebral body 2 and the lower engagement surface 308 to engage with the adjacent vertebral body 3. Alternatively, the upper engagement surface 306 and/or the lower engagement surface 308 can be curved convexly or concavely to allow for a greater or lesser degree of engagement with the adjacent vertebral bodies 2, 3. In an exemplary embodiment, the upper engagement surface 306 and/or the lower engagement surface includes texturing 312 to aid in gripping the adjacent vertebral bodies. Although not limited to the following, the texturing can include teeth, ridges, friction increasing elements, keels, or gripping or purchasing projections.

In an exemplary embodiment, vertically expanding plate 300 is coupled to an end of threaded bolt 318, which is coupled to the gear 302. In one embodiment, the threaded bolt 318 is in threaded engagement with the gear 302. In an alternative embodiment, a bolt having ratchet teeth may be used instead of threaded bolt 318. In an embodiment, the gear 302 is coupled to the landing 312. In one embodiment, the gear 302 is rotatably coupled to the landing 312.

Figure 23:
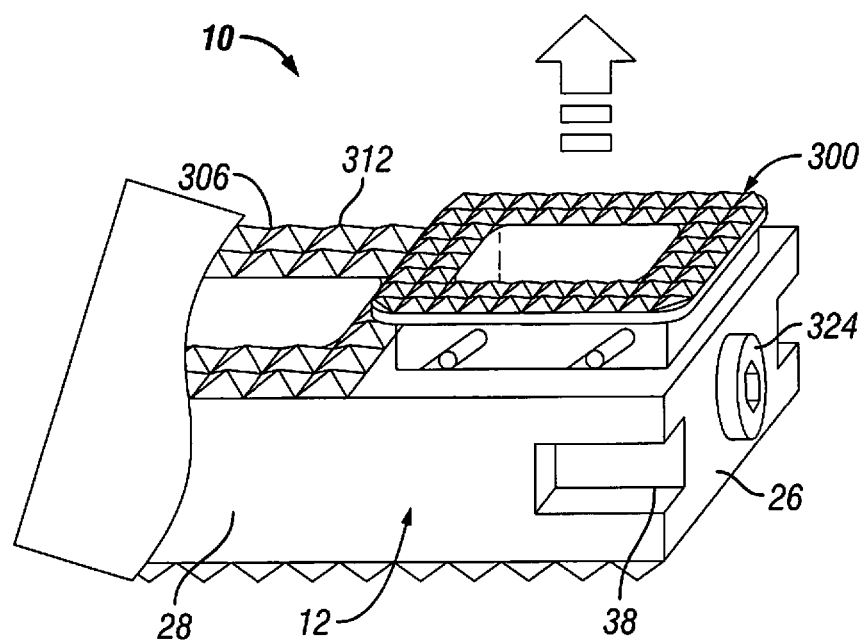
FIG. 23 is a perspective view of the expandable fusion device of FIG. 21 with a closed end.

The vertically expanding plate 300 includes a throughbore 319 and an upper surface 320. In one embodiment, the vertically expanding plate 300 is generally circular in shape. Other suitable configurations of the expanding plate 300 may also be suitable. In an embodiment, the vertically expanding plate may be generally rectangular in shape with rounded corners, as best seen in FIG. 23. In one embodiment, the vertically expanding plate 300 is flat and generally planar to allow upper surface 320 to engage with the adjacent vertebral body 2. Alternatively, the upper surface 320 can be curved convexly or concavely to allow for a greater or lesser degree of engagement with the adjacent vertebral bodies. In an exemplary embodiment, the upper surface 320 includes texturing 322 to aid in gripping the adjacent vertebral bodies. Although not limited to the following, the texturing can include teeth, ridges, friction increasing elements, keels, or gripping or purchasing projections.

With reference to FIG. 23, an alternative embodiment of the expandable fusion device 10 of FIGS. 21-22 is shown. In this embodiment, the gear 302 is enclosed within the body portion 12 towards the second end 26 of the body portion 12 with the vertically expanding plate 300 disposed at or above the upper engagement surface 306 of the body portion 12. In an embodiment, the vertically expanding plate 300 is positioned towards the second end 26 of the body portion 12. While not illustrated, the threaded bolt 318 extends through the upper engagement surface 306 and couples the vertically expanding plate 300 and the gear 302. An actuator screw 324 extends through the first end 24 of the body portion 12 to engage the gear 302.

Figure 24:
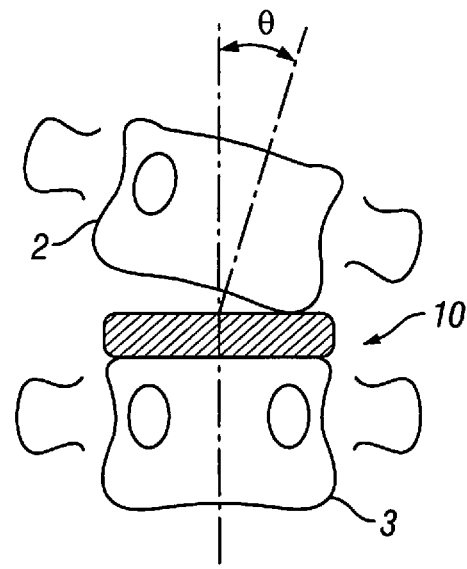
FIG. 24 is a front view of the expandable fusion device of FIG. 23 shown between adjacent vertebrae in an unexpanded position.
Figure 25:
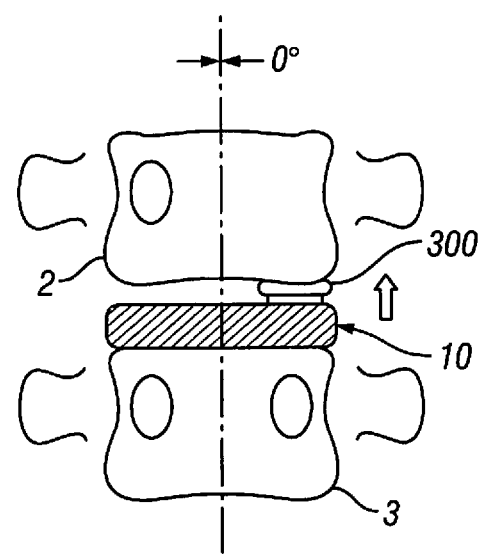
FIG. 25 is a front view of the expandable fusion device of FIG. 23 shown between adjacent vertebrae in an expanded position.

The expandable fusion device 10 of FIGS. 21-23 can be inserted in the intervertebral space in a manner similar to that the previously described with respect to FIGS. 1-6. FIG. 24 illustrates the expandable fusion device 10 of FIG. 23 between adjacent vertebral bodies 3, 4 in an unexpanded position. After insertion, the expandable fusion device 10 of FIGS. 21-23 can be expanded into the expanded position. As previously mentioned, a portion of the fusion device shown on FIGS. 21-23 expands vertically in at least one direction. To partially expand the fusion device 10, the gear 302 can be rotated in a first direction. An instrument 326 having a gear 328 disposed on a distal end 330 of the instrument may be used to rotate the gear 302, as best seen on FIG. 22. In another embodiment, an instrument (not illustrated) may be used to rotate actuation member 324 in a first direction. As discussed above, the actuation member 324 is engaged with gear 302; thus, as the actuation member 324 is rotated in first direction, the gear 302 rotated in a first direction. The embodiment with the actuation member 324 is best seen in FIG. 23. As the gear 302 rotates, the threaded bolt 318 extends outward from the gear 302, thus extending the laterally expanding plate 300 outward from the body portion 12. FIG. 25 illustrates the expandable fusion device 10 of FIG. 23 in an expanded position.

After expansion, the expandable fusion device 10 can be contracted back to the unexpanded position. The unexpanded position of the fusion device 10 is best seen in FIG. 24. To contract the fusion device 10, the gear 302 is rotated in a second direction that is opposite the first direction. The instrument 326 with the gear 328 may be used to rotate the gear 302. Alternatively, an instrument may be used to rotate the actuation member 324 to turn the gear 302 in the second direction. As the gear 302 rotates in the second direction, the threaded bolt 318 retracts pulling the laterally expanding plate 300 inward into the unexpanded position.

Although the preceding discussion only discussed having a single fusion device 10 in the intervertebral space, it is contemplated that more than one fusion device 10 can be inserted in the intervertebral space. It is further contemplated that each fusion device 10 does not have to be finally installed in the fully expanded state. Rather, depending on the location of the fusion device 10 in the intervertebral disc space, the height of the fusion device 10 may vary from unexpanded to fully expanded.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of installing an intervertebral implant, the method comprising:
   positioning the intervertebral implant between adjacent vertebrae, the intervertebral implant comprising a body portion with a first end and a second end, a first endplate having first and second ramped portions, an actuation member, and a translation member, the translation member comprising a first angled surface and a second angled surface;
   rotating the actuation member of the intervertebral implant in a first direction such that a distal face of the actuation member engages the translation member, wherein rotation of the actuation member moves the translation member in a first direction thereby causing the first angled surface to push against the first ramped surface of the first endplate and the second angled surface to push against the second ramped surface of the first endplate moving the first endplate in a direction away from the body portion into an expanded position,
   wherein the first and second angled surfaces are at a first distance from each other when the first endplate is in an unexpanded position and at a second distance in an expanded position, wherein the first and second distances are equal,
   wherein the actuation member is coupled to the translation member, the actuation member having a first end and a second end, the first end comprising an extension that is received within the translation member,
   wherein the extension of the actuation member comprises a lip portion, wherein the lip portion is received in a locking mechanism that extends from an expansion portion of the translation member, the locking mechanism comprising a slot configured to receive the lip portion of the extension and a stop configured to engage the lip portion when the lip portion is in the slot.

2. The method of claim 1, wherein the rotational movement of the actuation member results in generally linear movement of the translation member.

3. The method of claim 1, further comprising a pin member for securing the actuation member in the translation member, wherein the pin member is disposed through a central bore of the actuation member.

4. The method of claim 1, wherein the first endplate comprises an opening extending from the upper surface through the lower surface, wherein the upper surface of the first endplate comprises at least one texturing selected from the group consisting of teeth, ridges, friction increasing elements, keels, gripping projections, and purchasing projections.

5. The method of claim 1, wherein the translation member comprises a second expansion portion.

6. The method of claim 1, wherein the first angled surface is part of the expansion portion of the translation member, wherein the expansion portion engages the first endplate in a slotted fashion.

7. The method of claim 1, wherein portions of the first endplate extend in a generally oblique manner.

8. The method of claim 1, wherein first and second sides of the body portion each comprise a recessed portion configured and dimensioned for receiving an insertion instrument.

9. The method of claim 1, wherein the first end of the body portion includes at least one angled surface.

10. A method of installing an intervertebral implant, the method comprising:
    positioning the intervertebral implant between adjacent vertebrae, the intervertebral implant comprising a body portion with a first end and a second end, a first endplate having first and second ramped portions, an actuation member, and a translation member, the translation member comprising a first angled surface and a second angled surface;
    engaging a distal face of the actuation member with the translation member thereby moving the translation member in a first direction to thereby causing the first angled surface to push against the first ramped surface of the first endplate and the second angled surface to push against the second ramped surface of the first endplate moving the first endplate in a direction away from the body portion into an expanded position,
    wherein the first and second angled surfaces are at a distance from each other when the first endplate is in an unexpanded position and at a second distance in an expanded position, wherein the first and second distances are equal,
    wherein the actuation member is coupled to the translation member, the actuation member having a first end and a second end, the first end comprising an extension that is received within the translation member,
    wherein the extension of the actuation member comprises a lip portion, wherein the lip portion is received in a locking mechanism that extends from an expansion portion of the translation member, the locking mechanism comprising a slot configured to receive the lip portion of the extension and a stop configured to engage the lip portion when the lip portion is in the slot.

11. The method of claim 10, wherein the first endplate comprises an opening extending from the upper surface through the lower surface and wherein the upper surface of the first endplate comprises at least one texturing selected from the group consisting of teeth, ridges, friction increasing elements, keels, gripping projections, and purchasing projections.

12. The method of claim 10, wherein the first angled surface is part of the expansion portion.

13. The method of claim 10, wherein the first angled surface of the expansion portion engages the first endplate in a slotted fashion.

14. The method of claim 10, wherein portions of the first endplate extend in a generally oblique manner.

15. The method of claim 10, wherein first and second sides of the body portion each comprise a recessed portion configured and dimensioned for receiving an insertion instrument.

16. The method of claim 10, wherein the first end of the body portion includes at least one angled surface.

17. A method of installing an intervertebral implant, the method comprising:

positioning the intervertebral implant between adjacent vertebrae, the intervertebral implant comprising a body portion with a first end and a second end, a first endplate having first and second ramped portions, an actuation member, and a translation member, the translation member comprising a first angled surface and a second angled surface;

rotating the actuation member of the intervertebral implant in a first direction such that a distal face of the actuation member engages the translation member, wherein rotation of the actuation member moves the translation member in a first direction thereby causing the first angled surface to push against the first ramped surface of the first endplate and the second angled surface to push against the second ramped surface of the first endplate moving the first endplate in a direction away from the body portion into an expanded position, wherein the first and second angled surfaces are at a first distance from each other when the first endplate is in an unexpanded position and at a second distance in an expanded position, wherein the first and second distances are equal, wherein the actuation member is coupled to the translation member, the actuation member having a first end and a second end, the first end comprising an extension that is received within the translation member, the implant comprising a pin member for securing the actuation member in the translation member, wherein the pin member is disposed through a central bore of the actuation member.

18. The method of claim 17, wherein the extension of the actuation member comprises a lip portion, wherein the lip portion is received in a locking mechanism that extends from an expansion portion of the translation member, the locking mechanism comprising a slot configured to receive the lip portion of the extension and a stop configured to engage the lip portion when the lip portion is in the slot.

* * * * *